(12) United States Patent
Stock (10) Patent No.: US 7,264,971 B2
(45) Date of Patent: Sep. 4, 2007

(54) READ-HEAD FOR OPTICAL DIAGNOSTIC DEVICE

(75) Inventor: Nicholas T. Stock, Govilon (GB)

(73) Assignee: Siemens Medical Solutions Diagnostics, Tarrytown, NY (US)

( * ) Notice: Subject to any disclaimer, the term of this patent is extended or adjusted under 35 U.S.C. 154(b) by 346 days.

(21) Appl. No.: 10/894,849

(22) Filed: Jul. 20, 2004

(65) Prior Publication Data

US 2006/0018792 A1   Jan. 26, 2006

(51) Int. Cl.
  *G01N 21/01* (2006.01)
  *G01N 35/00* (2006.01)
  *G02B 26/10* (2006.01)

(52) U.S. Cl. .................. 436/165; 250/208.1; 250/226; 250/227.11; 250/227.26; 250/227.32; 250/234; 250/559.18; 356/218; 356/237.1; 356/446; 422/65; 422/66; 422/82.05; 422/82.06; 422/82.07; 422/82.08; 422/82.09; 422/82.11; 436/43; 436/44; 436/46; 436/63; 436/93; 436/94; 436/95

(58) Field of Classification Search ................ 356/218, 356/237.5, 402, 407, 411, 420, 446, 237.1; 250/208.1, 226, 227.11, 227.26, 227.32, 234–236, 250/559.18, 559.41; 385/12–13; 422/56–58, 422/63–67, 82.05–82.09, 82.11; 436/43–44, 436/46, 63, 66–67, 93–95, 165, 169
See application file for complete search history.

(56) References Cited

U.S. PATENT DOCUMENTS

| | | | | |
|---|---|---|---|---|
| 3,907,503 A | * | 9/1975 | Betts et al. | .................... 422/67 |
| 4,659,229 A | * | 4/1987 | Hernicz | ...................... 356/446 |
| 4,795,911 A | * | 1/1989 | Kohno et al. | .......... 250/559.18 |
| 5,143,694 A | * | 9/1992 | Schafer et al. | ................. 422/65 |
| 5,408,535 A | | 4/1995 | Howard, III et al. | |
| 5,449,898 A | * | 9/1995 | Dosmann | .................. 250/208.1 |
| 5,518,689 A | * | 5/1996 | Dosmann et al. | ........ 422/82.05 |
| 5,528,360 A | | 6/1996 | Kohno | ..................... 356/237.5 |
| 5,654,803 A | * | 8/1997 | Howard et al. | ............. 356/446 |
| 5,701,181 A | * | 12/1997 | Boiarski et al. | ............ 356/446 |
| 5,877,863 A | | 3/1999 | Ross et al. | |
| 2003/0098976 A1 | * | 5/2003 | Yamauchi | .................... 356/344 |

* cited by examiner

*Primary Examiner*—Arlen Soderquist
(74) *Attorney, Agent, or Firm*—Richard L. Sampson; Noam Pollack (57) ABSTRACT

A readhead for a photometric diagnostic instrument includes a housing adapted for incorporation within the photometric diagnostic instrument, and an elongated sample table operatively engaged with the housing. The sample table is configured to support elongated reagent sample media of the type having a plurality of test areas disposed in spaced relation thereon, each of the test areas being configured to react with a sample and to change color according to an amount of a constituent or property in the sample. A light source is provided to illuminate the sample table. An imager having an elongated field of view is coupled to the housing, the elongated field of view including at least a portion of the sample table. A scanning mechanism is configured to move the field of view relative to the sample table.

43 Claims, 7 Drawing Sheets

FIG. 5B
START OF AREA SCAN

FIG. 5C
END AREA SCAN

FIG. 5D
AREA SCANNED

READ-HEAD FOR OPTICAL DIAGNOSTIC DEVICE

BACKGROUND

1. Technical Field

The present invention generally relates to the field of clinical chemistry. More particularly, the present invention relates to a readhead for a diagnostic imaging system that analyzes the color change associated with one or more test areas on sample media following contact thereof with a liquid specimen, such as urine or blood.

2. Background Information

Throughout this application, various patents are referred to by an identifying citation. The disclosures of the patents referenced in this application are hereby incorporated by reference into the present disclosure.

Sample media such as reagent test strips are widely used in the field of clinical chemistry. A test strip usually has one or more test areas spaced along the length thereof, with each test area being capable of undergoing a color change in response to contact with a liquid specimen. The liquid specimen usually contains one or more constituents or properties of interest. The presence and concentrations of these constituents or properties are determinable by an analysis of the color changes undergone by the test strip. Usually, this analysis involves a color comparison between the test area or test pad and a color standard or scale. In this way, reagent test strips assist physicians in diagnosing the existence of diseases and other health problems.

Color comparisons made with the naked eye can lead to imprecise measurement. Today, strip reading instruments exist that employ reflectance photometry for reading test strip color changes. These instruments accurately determine the color change of a test strip within a particular wavelength range or bandwidth. Some instruments may also measure color inconsistencies outside this bandwidth. For example, instruments such as those sold under the CLINITEK® trademark by Bayer Healthcare Diagnostics Division of Bayer HealthCare LLC (Medfield, Mass.) and/or as disclosed in U.S. Pat. Nos. 5,408,535 and 5,877,863 (the '863 patent), both of which are fully incorporated by reference herein, may detect features such as traces of blood within a urine specimen on a MULTISTIX® (Bayer) reagent strip. After the urine specimen contacts the test pad of a MULTISTIX® reagent strip, intact blood cells appear as small green blotches on the yellow test area. These existing strip readers can detect both the overall color of the test pad and the small blotches of green.

As disclosed in the '863 patent, these instruments typically include a Readhead configured to illuminate the test strip and enable images of the illumined test strip to be captured by one or more imagers or detectors such as CCD devices and the like. These imagers tend to be elongated, having a relatively high aspect ratio (ratio of length to width). The high aspect ratio advantageously provides these imagers with a field of view that is sufficiently elongated to capture images of nominally along the entire length of the elongated test strips.

A trade-off, however, associated with these high aspect ratio imagers is that the field of view tends to be relatively narrow, to thus capture a similarly narrow image. The captured image typically represents only a small slice or fraction of the total test area of the test strip. Although this 'slice' is generally sufficient to generate useful test results, increased image width may be desirable in many applications, such as to increase the dynamic range of the instrument for improved resolution. Although larger CCD devices may be used to capture wider images, a CCD large enough to capture an image of nominally the entire length and width of the test strip may be prohibitively expensive.

A need therefore exists for an improved diagnostic testing device that efficiently expands the width of an image captured with a high aspect ratio imager.

SUMMARY

One aspect of the present invention includes a readhead for a photometric diagnostic instrument for illuminating a target area and receiving light from the target area. The readhead includes a housing adapted for incorporation within the photometric diagnostic instrument, and a first light source configured to emit light of a first wavelength. A second light source is also coupled to the housing, and is configured to emit light of a second wavelength. An elongated sample table is also provided, which has an aspect ratio of longitudinal to transverse dimension of at least 2:1. The sample table is configured to support elongated reagent sample media having a plurality of test areas disposed in spaced relation thereon, each of the test areas being configured to react with a sample and to change color according to an amount of a constituent or property in the sample. A light guide is disposed to receive light from each of the light sources, and to convey, when only one of the light sources is illuminated, substantially all of the light from the one light source towards the sample table. An elongated image capture device receives light from the target area, and has an aspect ratio of longitudinal to transverse dimension of at least 2:1. A scanning mechanism is configured to move an image of the sample table relative to the image capture device.

In another aspect of the invention, a readhead for a photometric diagnostic instrument includes a housing adapted for incorporation within the photometric diagnostic instrument, and an elongated sample table operatively engaged with the housing. The sample table is configured to support elongated reagent sample media of the type having a plurality of test areas disposed in spaced relation thereon, each of the test areas being configured to react with a sample and to change color according to an amount of a constituent or property in the sample. A light source is provided to illuminate the sample table. An imager having an elongated field of view is coupled to the housing, the elongated field of view including at least a portion of the sample table. A scanning mechanism is configured to move the field of view relative to the sample table.

Another aspect of the invention includes a photometric diagnostic instrument. This instrument includes a housing and an elongated sample table operatively engaged with the housing. The sample table is configured to support elongated reagent sample media in a predetermined orientation thereon, the sample media having a plurality of test areas disposed in spaced relation thereon. Each of the test areas is configured to react with a sample and to change color according to an amount of a constituent or property in the sample. A light source is configured to illuminate the sample table. An elongated imager having an elongated field of view is coupled to the housing, in which the elongated field of view includes at least a portion of the sample table. A scanning mechanism is configured to move the field of view relative to the sample table. The imager is configured to capture an image of a portion of the sample media disposed within the field of view. A memory device is coupled to the imager, and a processor is coupled to the memory device and to the imager. The processor is configured to operate the scanning mechanism, and the imager is configured to capture images of portions of the sample media during movement of the field of view relative to the sample table. The memory device is configured to store captured images to form a composite image, and the processor is configured to analyze the composite image. The processor is also configured to derive a diagnosis value from the analysis, and to generate an output corresponding thereto.

A further aspect of the invention includes a method for reading reagent sample media of the type having a plurality of test areas disposed in spaced relation thereon, each of the test areas configured to react with a sample and to change color according to an amount of a constituent or property in the sample. The method includes receiving the sample media into a sample table associated with a readhead of a photometric diagnostic device, the sample table configured to maintain the sample media in a predetermined orientation thereto. The method further includes moving a field of view of the imager relative to the sample table, capturing images of the test areas with the imager during the movement, and aggregating the images to form a composite image. The amount of the constituent or property in the sample is then derived from the analysis. An output signal corresponding to the amount is then generated.

A still further aspect of the invention includes a readhead for a photometric diagnostic instrument. The readhead includes housing means for incorporation within the photometric diagnostic instrument, and elongated sample table means for supporting elongated reagent sample media having a plurality of test areas disposed in spaced relation thereon. Each of the test areas is configured to react with a sample and to change color according to an amount of a constituent or property in the sample. The instrument also includes means for illuminating the sample table means, and imaging means coupled to the housing means. The imaging means has an elongated field of view which includes at least a portion of the sample table means. Scanning means is also included for moving the field of view relative to the sample table.

A yet further aspect of the invention includes a photometric diagnostic instrument including means for housing the diagnostic instrument, and elongated sample table means for supporting elongated reagent sample media in a predetermined orientation thereon. The sample media has a plurality of test areas disposed in spaced relation thereon, each of the test areas configured to react with a sample and to change color according to an amount of a constituent or property in the sample. The instrument also includes illumination means for illuminating the sample table means, and imaging means for capturing an image of a portion of the sample media disposed within an elongated field of view. The elongated field of view includes at least a portion of the sample table means. Scanning means is included for moving the field of view relative to the sample table means. Memory means is provided for storing captured images to form a composite image. Processing means are coupled to the memory device, the imaging means, and the scanning means, for operating the imaging means, the memory means, and the scanning means. The imaging means is adapted for capturing images of portions of the sample media during the movement of the field of view relative to the sample table. The processing means is adapted for analyzing the composite image, for deriving a diagnosis value from the analysis, and for generating an output corresponding thereto.

BRIEF DESCRIPTION OF THE DRAWINGS

The above and other features and advantages of this invention will be more readily apparent from a reading of the following detailed description of various aspects of the invention taken in conjunction with the accompanying drawings, in which:

FIG. 5C is a view similar to those of FIGS. 5A-5C, of a composite image formed by embodiments of the present invention;

DETAILED DESCRIPTION

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following detailed description is, therefore, not to be taken in a limiting sense, and the scope of the present invention is defined by the appended claims and their equivalents. For clarity of exposition, like features shown in the accompanying drawings are indicated with like reference numerals and similar features as shown in alternate embodiments in the drawings are indicated with similar reference numerals.

Figure 1:
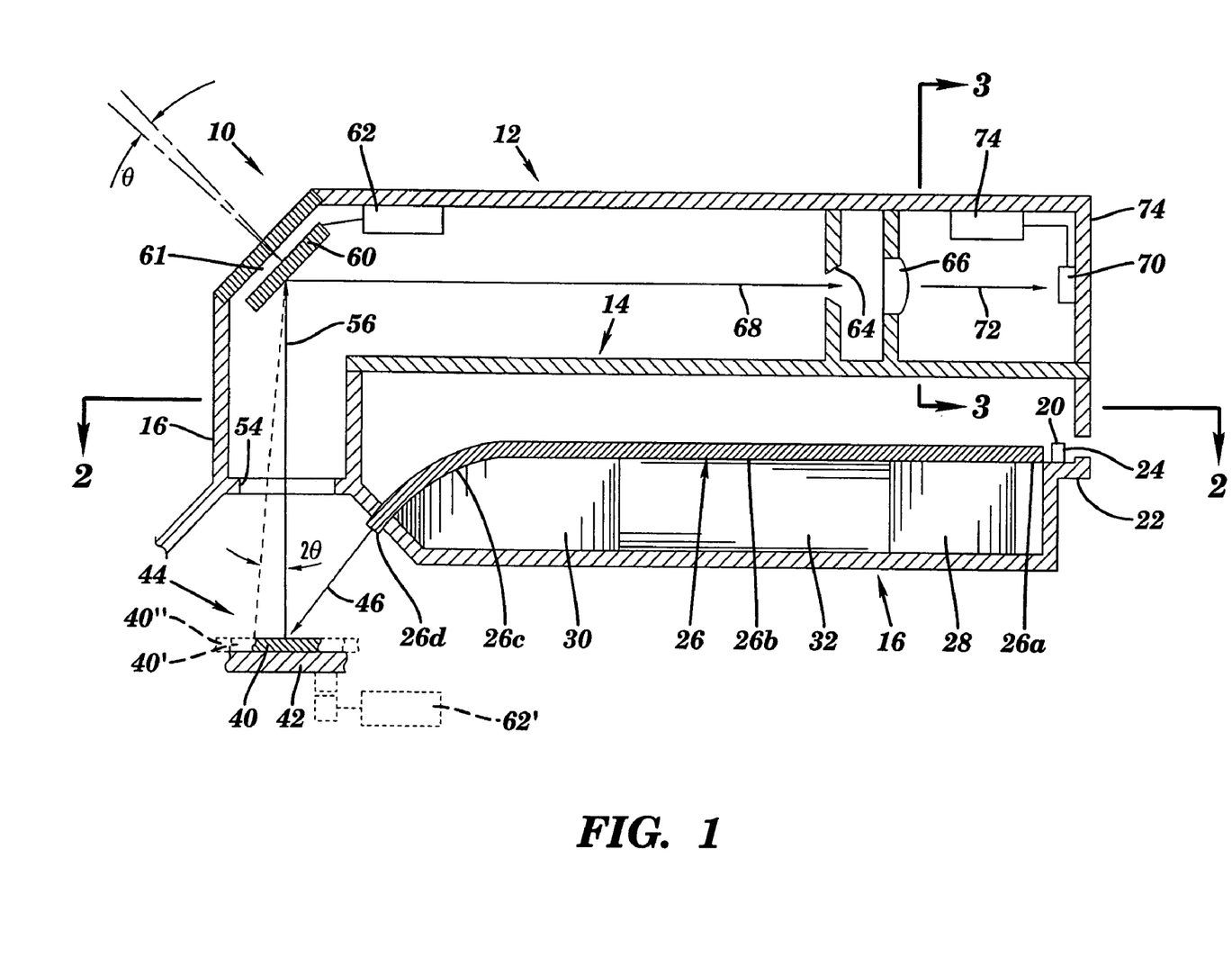
FIG. 1 is an elevational schematic view of an embodiment of the present invention, with alternative aspects shown in phantom.
Figure 2:
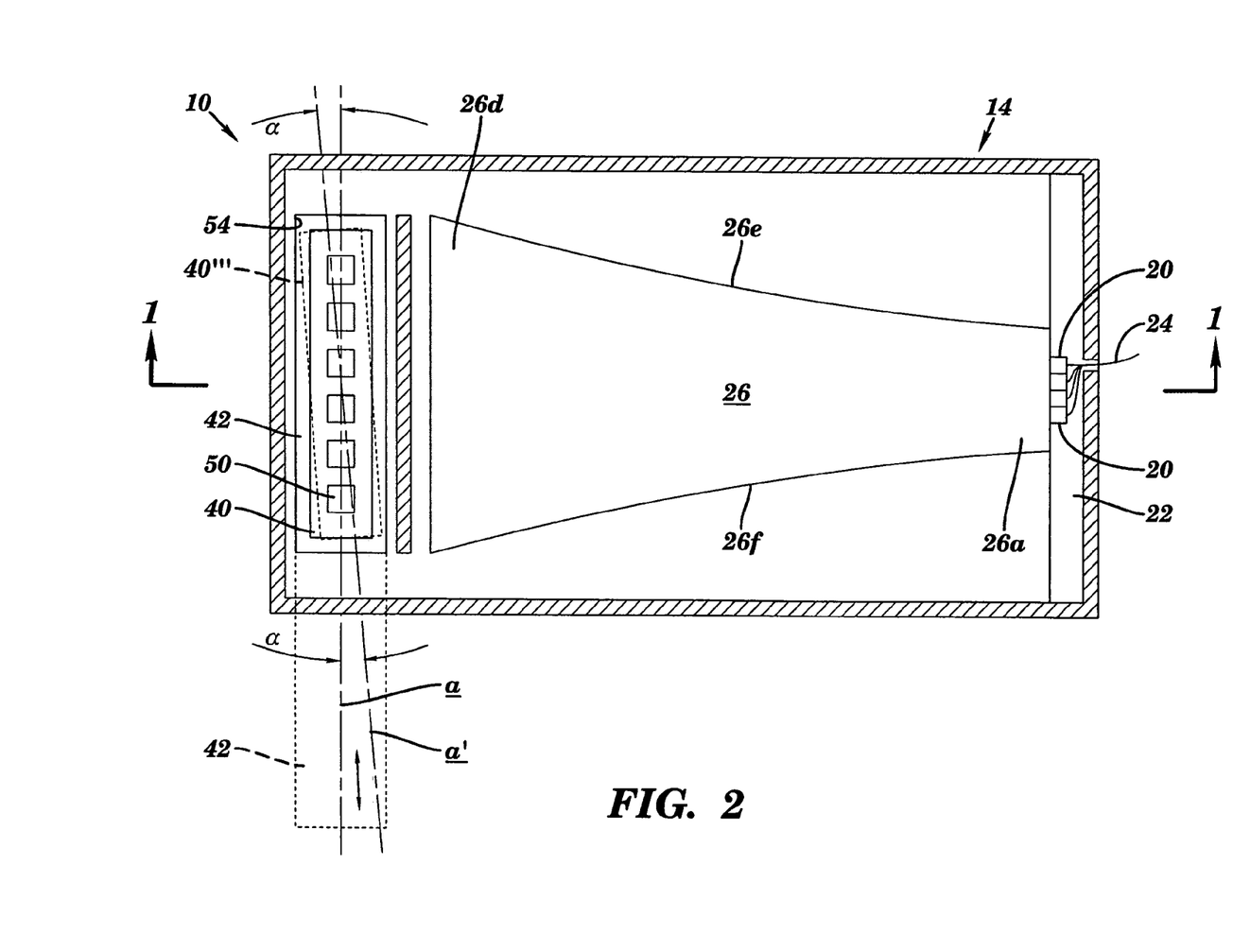
FIG. 2 is a cross-sectional view taken along 2-2 of FIG. 1, with alternative aspects shown in phantom.
Figure 3:
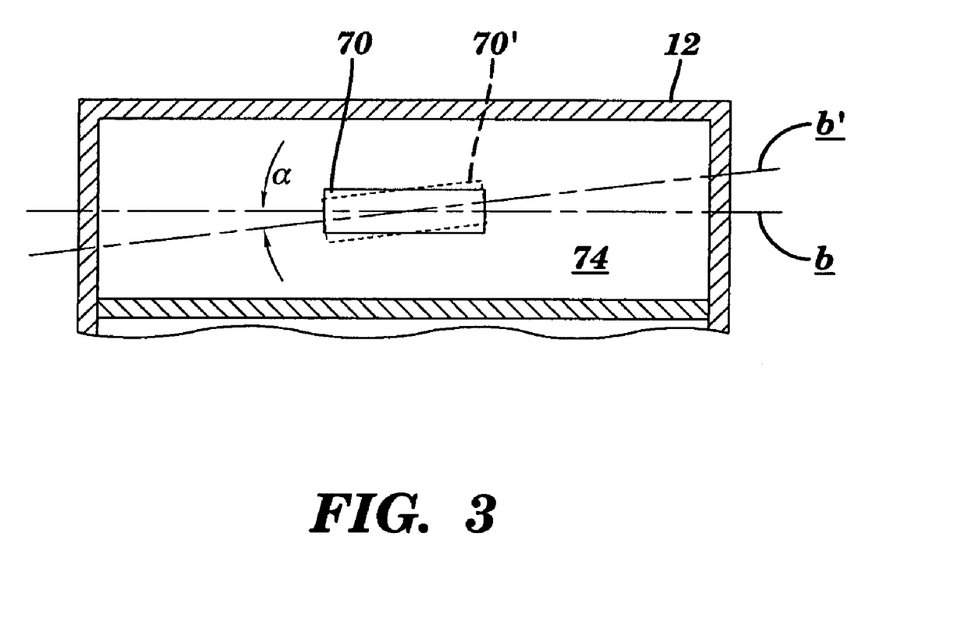
FIG. 3 is a cross-sectional view taken along 3-3 of FIG. 1, aspects of an alternative embodiment shown in phantom.

An overview of an embodiment of the invention is provided with reference to FIGS. 1-3. This embodiment includes a read-head 10 for a photometric diagnostic instrument of the type used to analyze reagent sample media, e.g., for the above-referenced CLINITEK® instrument. Read-head 10 is provided with a scanning mechanism configured to conveniently scan an image of an elongated sample media 40 transversely across an elongated image capture device (or detector) 70. Detector 70 may thus capture a series of images of portions of the sample media 40 that may be combined, e.g., by saving the images to memory 74, to form a composite image of sample media 40.

In one embodiment, the scanning mechanism includes a mirror 60 pivotably disposed optically between the target area and the image capture device. An actuator 62 is configured to selectively pivot mirror 60 to scan the image relative to image capture device 70.

In another embodiment, the scanning mechanism includes a image capture device 70', having a field of view 72''' (FIG. 5A) oriented at an oblique angle relative to sample media 40. An actuator 62' is configured to slide sample table 42 (and sample media disposed thereon) alternately into and out of field of view 72''', e.g., in a direction substantially parallel to longitudinal axis $\underline{a}$ of sample media 40 as shown in FIG. 2.

As is familiar to those skilled in the art, sample media 40 may include typical urine analysis strips, having paper pads disposed in spaced relation thereon, which are soaked in chemical reagents that react with a specimen sample to change color according to the medical condition of the patient, i.e., according to an amount of constituent or property in the sample. Examples of such media 40 include the aforementioned MULTISTIX® test strips. Alternatively, sample media 40 may include a conventional immuno-assay cassette, e.g., the CLINITEST® hCG cassette (Bayer), (such as shown schematically in phantom as 40' in FIG. 1), having an area soaked in chemical reagents that react to the sample to reveal a colored line or pattern of lines according to the medical condition of the patient.

Other suitable sample media may include conventional microfluidic devices (such as shown schematically as 40" in FIG. 1) which typically include a substrate having a series of narrow channels, e.g. on the order of microns in width, through which a fluid such as blood or urine may travel. The channels conduct the fluid to various test areas on the device. These devices enable various tests to be performed using only a small amount of fluid, e.g., using a small drop of liquid. Exemplary microfluidic devices are described in U.S. patent application Ser. No. 10/082,415 filed on Feb. 26, 2002 and entitled Method and Apparatus For Precise Transfer And Manipulation of Fluids by Centrifugal and or Capillary Forces.

For convenience and clarity, various embodiments of the present invention are described as using sample media 40 in the form of MULTISTIX® test strips, with the understanding that substantially any form of sample media may be used without departing from the spirit and scope of the present invention. Embodiments of the present invention may be particularly beneficial when used with alternate media such as immuno-assay cassettes due to their often faint or otherwise difficult to read results. The composite images of the present invention advantageously improve the signal to noise ratio and thus the reliability and accuracy relative to the prior art.

Where used in this disclosure, the term "longitudinal" refers to a direction relative to an element, which is substantially parallel to its long axis $\underline{a}$, $\underline{b}$, $\underline{b'}$ (FIGS. 2 & 3) when the element is installed on a readhead 10 of the present invention. Similarly, the term "transverse" refers to a direction substantially orthogonal to the longitudinal direction.

Software associated with the various embodiments of the present invention can be written in any suitable language, such as C++; Visual Basic; Java; VBScript; Jscript; BCMAscript; DHTMl; XML and CGI. Any suitable database technology may be employed, including but not limited to versions of Microsoft Access and IMB AS 400.

Particular embodiments of the present invention will now be described in detail. Turning to FIGS. 1-3, embodiments of the present invention include a readhead 10 for a photometric diagnostic instrument such as a CLINITEK® reflectance spectroscope. Readhead 10 has a housing which may be formed from an upper housing portion 12, a middle housing portion 14, and a lower housing portion 16, which may be fastened to one another in any conventional manner. While these housing portions 12, 14, 16 are shaped and adapted to be incorporated into a photometric diagnostic instrument, the particular configuration of housing portions 12, 14, 16 is not considered important to the invention, and modifications thereto may be made, such as to facilitate the integration thereof into the diagnostic instrument, may be made without departing from the spirit and scope of the present invention.

As shown, light sources, e.g., in the form of light-emitting diodes (LEDs) 20 are disposed in the housing, e.g., supported on a ledge 22 formed in the lower housing portion 16. The LEDs 20 are configured to operate in a conventional manner, e.g., by selectively emitting monochromatic radiation of mutually distinct wavelengths, such as corresponding to red light, green light, blue light and infrared light.

The LEDs 20 are disposed to radiate light into an inlet end 26a of a light guide 26, where it passes through mid portions 26b and 26c, before exiting at outlet end 26d of the light guide 26. As shown in FIG. 2, an exemplary light guide 26 includes curved sides 26e, 26f that diverge outwardly from inlet end 26a to outlet end 26d. Light guide 26 may be supported by any suitable supports, such as by supports 28 and 30.

As shown in FIG. 1, light is emitted from the outlet end 26d of the light guide 26 onto sample media 40 disposed on a sample table 42 within a target area 44, as indicated by arrow 46. In this embodiment, target area 44 is generally defined by opening 54 as shown in FIG. 2, described below. In the embodiment shown, sample media 40 includes a reagent strip having a predetermined number of test areas (e.g., reagent pads) 50 thereon. Each reagent pad 50 includes a relatively absorbent material impregnated with a respective reagent, each reagent and reagent pad 50 being associated with a particular test to be performed. When urinalysis tests are performed, they may include, for example, a test for leukocytes in the urine, a test of the pH of the urine, a test for blood in the urine, etc. When each reagent pad 50 comes into contact with a urine sample, the pad changes color, depending on the reagent used and the characteristics of the sample. As discussed above, reagent strip 40 may be a MULTISTIX® reagent strip commercially available from Bayer Corporation. As also mentioned above, the sample media may alternatively include an immuno-assay cassette 40' or a microfluidic device 40" as shown in phantom.

Light from the reagent strip 40 may pass through an opening 54 formed in the lower housing portion 16, which generally defines in a direction indicated by an arrow 56, towards a mirror 60 supported, for example, in housing portion 12. Mirror 60 may extend approximately the length of aperture 54 shown in FIG. 2. Mirror 60 reflects light incident thereon from the sample media 40 through an aperture 64 formed in housing portion 14 and to a lens 66, as indicated by an arrow 68. In the embodiment shown, one side of the lens 66 is substantially planar, while the other side of the lens 66 is convexly curved (aspheric). Light passing through the lens 66 is transmitted to detector 70, as indicated by an arrow 72.

Figure 4A:
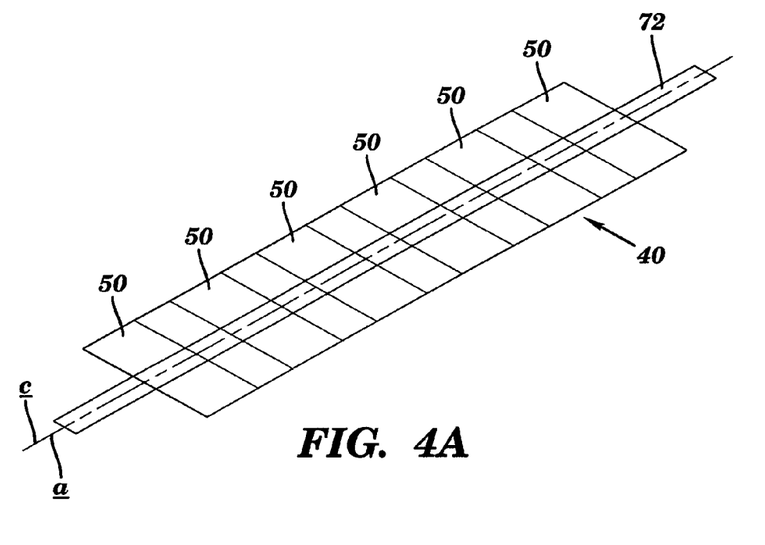
FIG. 4A is a perspective, schematic view of sample media superimposed with a representation of the field of view of an embodiment of FIGS. 1-3.

As shown in FIGS. 1 and 3, detector 70, which, e.g., is fixed to a side wall 74 of housing portion 12, may include a conventional detector, such as the ILX511 detector commercially available from Sony Corporation. This detector includes a single row of 2048 pixels aligned in a single row. As such, detector 70 has a relatively high aspect ratio (longitudinal to transverse dimension) as discussed above. This high aspect ratio advantageously provides detector 70 with a field of view 72 (FIG. 4A) of sufficient length to capture an image of nominally the entire length, including each individual test area 50, of high aspect ratio sample media 40 as shown in FIG. 4A. As used herein, the term 'high aspect ratio' refers to an aspect ratio of at least about 2:1, and in particular embodiments, greater than about 50:1. In embodiments using the aforementioned Sony ILX511 detector, which is 28.7 mm long by 0.2 mm wide, the aspect ratio is 143.5:1, while other commercial detectors have provided aspect ratios of 256:1.

Figure 4B:
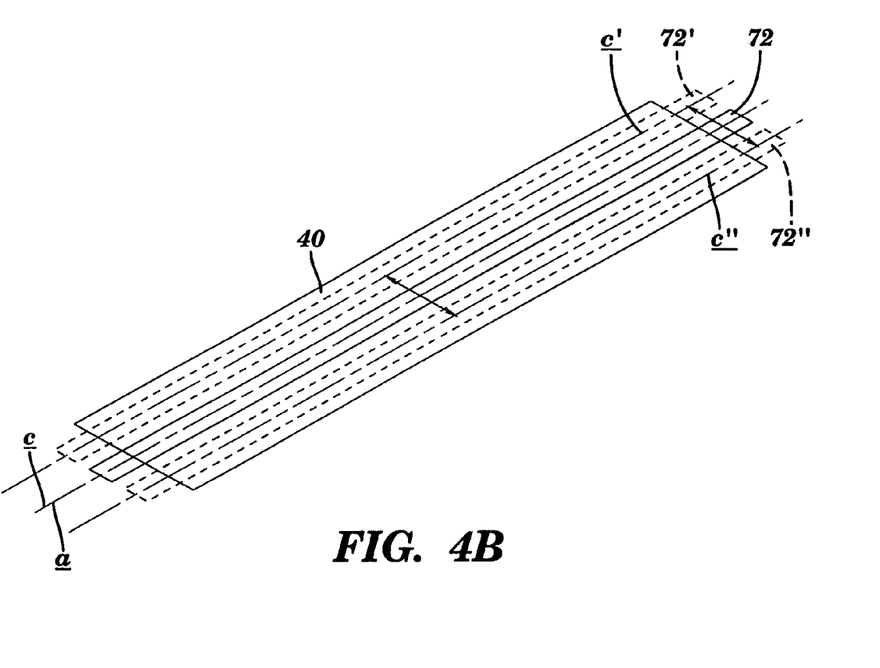
FIG. 4B is a view similar to that of FIG. 4A, showing alternate fields of view generated by embodiments of the present invention.

In this embodiment, detector 70 is disposed so that its longitudinal axis b (FIG. 3) is substantially parallel to longitudinal axis a (FIGS. 2, 4A-4B) of sample media 40. This configuration maintains the longitudinal axes c, c', C" of fields of view 72, 72', 72" nominally parallel to axis a of sample media 40 as shown in FIGS. 4A and 4B.

However, as also shown, these fields of view tend to be relatively narrow (i.e., in the transverse dimension). Thus, images captured by detector 70 generally represent only a small 'slice' or fraction of the total test area of the test strip 40, e.g., a fraction of the combined area of all test pads 50 in the embodiment shown. Embodiments of the present invention advantageously expand the effective width of images captured with high aspect ratio detectors 70 through the use of efficient scanning mechanisms. These scanning mechanisms enable the field of view 72 of a detector 70 to be moved transversely relative to the sample media 40 (or vice versa), such as shown at 72' and 72" of FIG. 4B.

Images within these fields of view may be captured, stored to a conventional memory device 74 (discussed below) and aggregated into a larger composite image that may be analyzed in a conventional manner by the diagnostic instrument (e.g., a CLINITEK® instrument) to which readhead 10 is operatively engaged. The use of these composite images serves to advantageously increase the dynamic range of the instrument for improved resolution, to effectively enable the instrument to achieve more accurate results than those of the prior art.

Those skilled in the art will recognize that storing the individual captured images 72, 72', 72", etc., to memory 74 to form a composite image is well within the skill in the art, and may be easily accomplished by simple modification of the operating software of, e.g., the CLINITEK® instrument.

In operation, the LEDs 20 are illuminated, typically one at a time, and the illumination provided by that single LED 20 illuminates the reagent strip 40 to an extent that allows the detector 70 to detect enough light from the reagent strip 40 to have various reagent tests, e.g., as described above, satisfactorily performed. Each individual image capture device or pixel in the detector 70 senses light from a particular location along the length of the reagent strip 40. For example, to detect light from the lowermost reagent pad 50 shown in FIG. 2, one or more of the image capture devices on the corresponding end of the detector 70 would be activated. In particular embodiments, light from all of the reagent pads 50 is simultaneously detected by activating all of the detectors in the detector 70.

Referring to FIGS. 1, 4A & 4B, one embodiment of a scanning mechanism of the present invention is shown. This embodiment includes mounting mirror 60 so that it may pivot relative to housing 12, such as by use of a hinge or gimble mount 61. Mirror 60 may also be coupled to a suitable actuator 62, which may include a conventional stepper motor, linear actuator, or the like. Actuator 62 may thus be used to selectively pivot mirror 60 to various angular positions θ as shown, each of which may be predetermined to present a distinct field of view 72, 72', 72" (FIGS. 4A, 4B)
to detector 70. In the particular embodiment shown, each angular increment θ of mirror 60 moves the field of view by approximately 2θ. For convenience, actuator 62 may be controlled by a processor, such as the processor(s) (not shown) used to control operation of the diagnostic device (e.g., the aforementioned CLINITEK® instrument) to which readhead 10 is operatively engaged. For example, referring to Table I, the operating system (OS) of the CLINITEK® instrument may be easily modified to signal 80 the actuator to move mirror 60 to a predetermined position corresponding to field of view 72. The OS may then actuate detector 70 to capture 82 an image of the field of view, and store 84 the image to memory 74. Steps 80-84 may then be repeated (at 86) for fields of view 72' and 72", etc., to form a sufficiently detailed composite image in memory 74. Thereafter, the OS may operate the instrument in a conventional manner to analyze 88 the stored composite image.

TABLE I

| | |
|---|---|
| 80 | Move mirror 60 to field of view 72 |
| 82 | Capture image of field of view 72 |
| 84 | Store the image to memory 74 |
| 86 | Repeat steps 80-84 for additional fields of view (e.g., 72' and 72", etc.) to form composite |
| 88 | Analyze composite image |

Alternate embodiments of the aforementioned scanning mechanism are shown in phantom in FIGS. 1-3, and with respect to FIGS. 5A-5D. In these embodiments, rather than pivoting a mirror 60, the detector and sample media are disposed obliquely relative to one another. This may be accomplished, for example, by mounting detector 70' (FIG. 3) so that its longitudinal axis b' is disposed at an angle α relative to that of detector 70 described above.

Figure 5A:
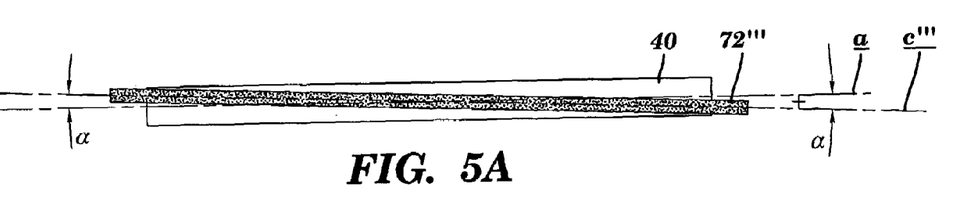
FIG. 5A is a plan schematic view of sample media superimposed with a representation of the field of view of an alternate embodiment of FIGS. 1-3.
Figure 5B:
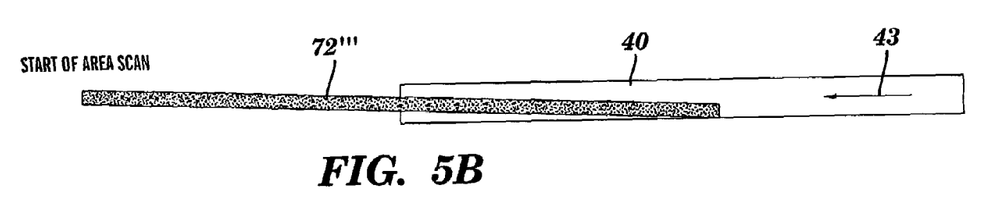
FIGS. 5B and 5C are views similar to that of FIG. 5A, taken during operation of the alternate embodiment of FIGS. 1-3.
Figure 5C:
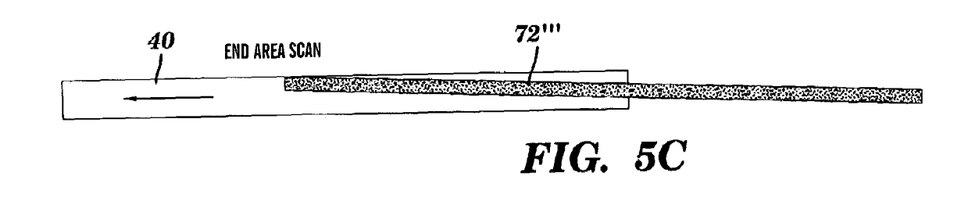

As best shown in FIG. 5A, this configuration effectively disposes the field of view 72''' of detector 70' at an oblique angle α to sample media 40. (See for example, axis c''' of field of view 72''' relative to axis a of sample media 40). As discussed above, actuator 62' (shown in phantom in FIG. 1), which may include a conventional stepper motor or linear actuator, is configured to slide sample table 42 (and sample media 40 disposed thereon) alternately into and out of field of view 72''', such as shown in FIGS. 5B & 5C.

Figure 5D:
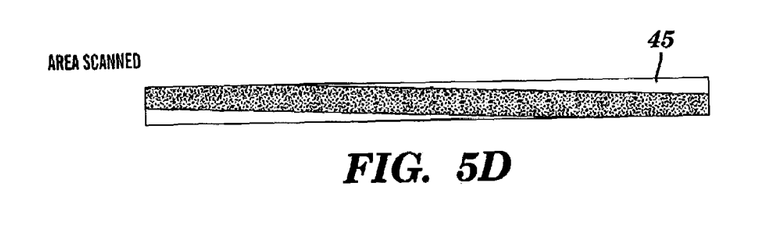

This obliquely angled orientation enables various unique images of media 40 to be captured as the tray moves relative to the field of view 72''', e.g., as tray 42 is inserted into housing portion 16. For example, tray 42 may be provided with a range of motion that extends from the position shown in FIG. 5B, to the position shown in FIG. 5C. Actuator 62' (FIG. 1) may be used to sequentially move tray 42 through this range of motion. Thus, referring to Table II, this embodiment may be operated by using actuator 62' to move 90 the sample media to a predetermined position within field of view 72'''. Detector 70' may then be actuated to capture 92 an image of the field of view, which is stored 94 to memory. Steps 90-94 may be repeated 96, with the tray 42 (and sample media 40) disposed at various distinct positions within its range of motion, to form a composite image 45, such as shown in FIG. 5D. The composite image 45 may be analyzed 98 as discussed above.

TABLE II

| | |
|---|---|
| 90 | Move sample media to position within field of view 72''' |
| 92 | Capture image of field of view 72''' |
| 94 | Store the image to memory 74 |

TABLE II-continued

| 96 | Repeat steps 90-94 for additional media positions within field of view 72''' to form composite |
| 98 | Analyze composite image |

As shown, the total area of media 40 captured within composite image 45 is substantially greater than that of a single image, such as shown in FIG. 5A. In other words, use of oblique angle α enables individual pixels of detector 70' to capture unique images of sample media 40, i.e., images of distinct portions of the sample media as it is moved through the field of view 72'''. Conversely, in the event the sample media 40 was not angled relative to the field of view, images captured during insertion would not be entirely unique. Rather, the same portions of the strip would disadvantageously be captured repeatedly by various pixels during this movement.

Although angle α is shown and described as being provided by disposing detector 70' at an angle relative to that of detector 70, those skilled in the art should recognize that any configuration that places the field of view of the detector at an angle α to sample media 40 may be used without departing from the spirit and scope of the present invention. For example, sample media shown in phantom as 40''' in FIG. 2, may be disposed at an angle α relative to tray 42 within which it is disposed, while using (non-angled) detector 70 as described above. Alternatively, both the detector and the sample media may be angled to provide a total relative angle α therebetween, without departing from the spirit and scope of the present invention.

Memory 74 may include any suitable device known to those skilled in the art, including RAM, ROM, and/or EPROM devices. Memory 74 may be a discrete device as shown, or alternatively, the memory device(s) associated with the conventional (e.g., CLINITEK®) instrument may be used for the purposes described herein.

Moreover, any suitable means may be provided to limit the range of motion of actuators 62, 62', including optical, electronic, mechanical, or electromechanical sensors. For example, conventional limit switches may be used to define the range of movement of actuators 62, 62'. Alternatively, detector 70, 70' may be used to limit the range of motion of the actuators 62, 62'. For example, captured images may be stored to memory only when the detector detects one or more predetermined features of the sample media 40 within its field(s) of view.

Moreover, although LEDs 20 are disclosed as exemplary light sources, those skilled in the art should recognize that nominally any device capable of generating sufficient light for detector 70, 70' to operate. Examples of suitable light sources 20 include one or more LEDs, VCSELs, incandescent lamps (e.g. tungsten), and/or laser emitting devices, such as solid state lasers etc. Alternatively, it may even be possible for particular embodiments of the present invention to simply utilize ambient light (e.g., sunlight), e.g., with appropriate light filtering.

Figure 6:
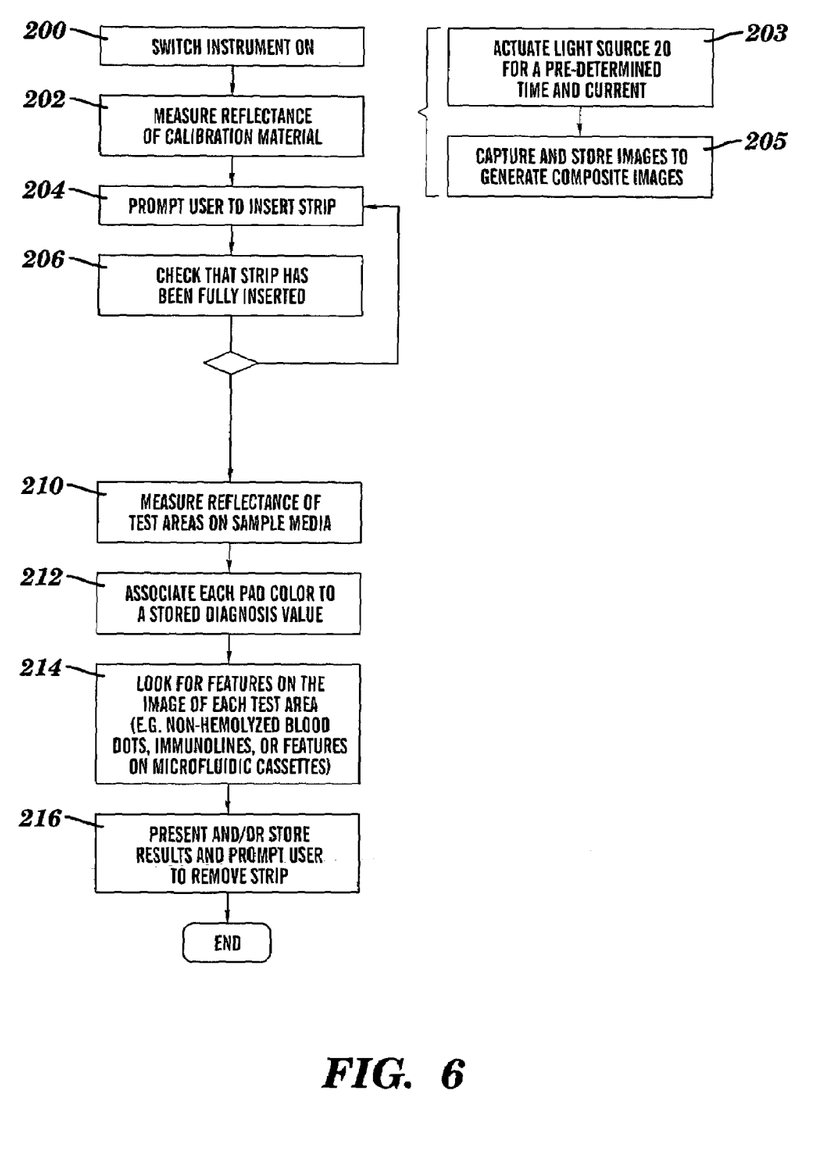
FIG. 6 is a flow chart of operational aspects of embodiments of the present invention.

Various operational aspects of the present invention have been described hereinabove. Additional operational aspects are substantially similar to those of conventional photometric diagnostic instruments such as the above-referenced CLINITEK® instrument, and/or as described in U.S. Provisional Patent Application Ser. No. 60/550,811, entitled Handheld Optical Diagnostic Device Having Image System Array, filed Mar. 5, 2004, which is fully incorporated herein by reference. Such operational aspects are briefly described with respect to FIGS. 6 & 7. Turning to FIG. 6, the instrument, including readhead 10 is initially powered up at 200, after which reflectance of calibration material is measured at 202. Calibration 202 may be effected automatically, e.g., each time the instrument is powered up 200, or may be initiated by the user, for example, in response to an audible or visual prompt.

Calibration 202 includes actuating or otherwise exposing the calibration material to light source(s) 20 for a pre-determined time and pre-determined current (e.g., when using an electrically actuated source 20) at 203, and capturing and storing images to generate a composite image of the calibration material (per Tables I and/or II above) at 205. These calibration images are used to effect sample measurement 210 as discussed in detail below with respect to FIG. 7.

Once calibration is complete, the instrument may prompt the user to insert sample media 40, 40', 40'' at step 204. Upon insertion, at 206, the system checks for an appropriate signal, e.g., from imager 70, 70', indicating that sample 40 has been fully inserted. If this signal has not been received, then the system loops back to step 204 to re-prompt the user to fully insert the sample. If the signal was received, then reflectance is measured 210 (described in greater detail below with respect to FIG. 7), and compared calibration values generated during calibration 202.

At 212, these reflectance values (colors) are compared to known diagnosis values stored in memory. At 214, images captured during measurement 210 are examined to identify any additional features such as non-hemolyzed blood dots or immunolines such as test lines on immunoassays, and then compared with known diagnosis values. At 216, results (i.e., diagnosis values) generated by steps 212 and/or 214 are then outputted to a display and/or stored to memory 62.

Figure 7:
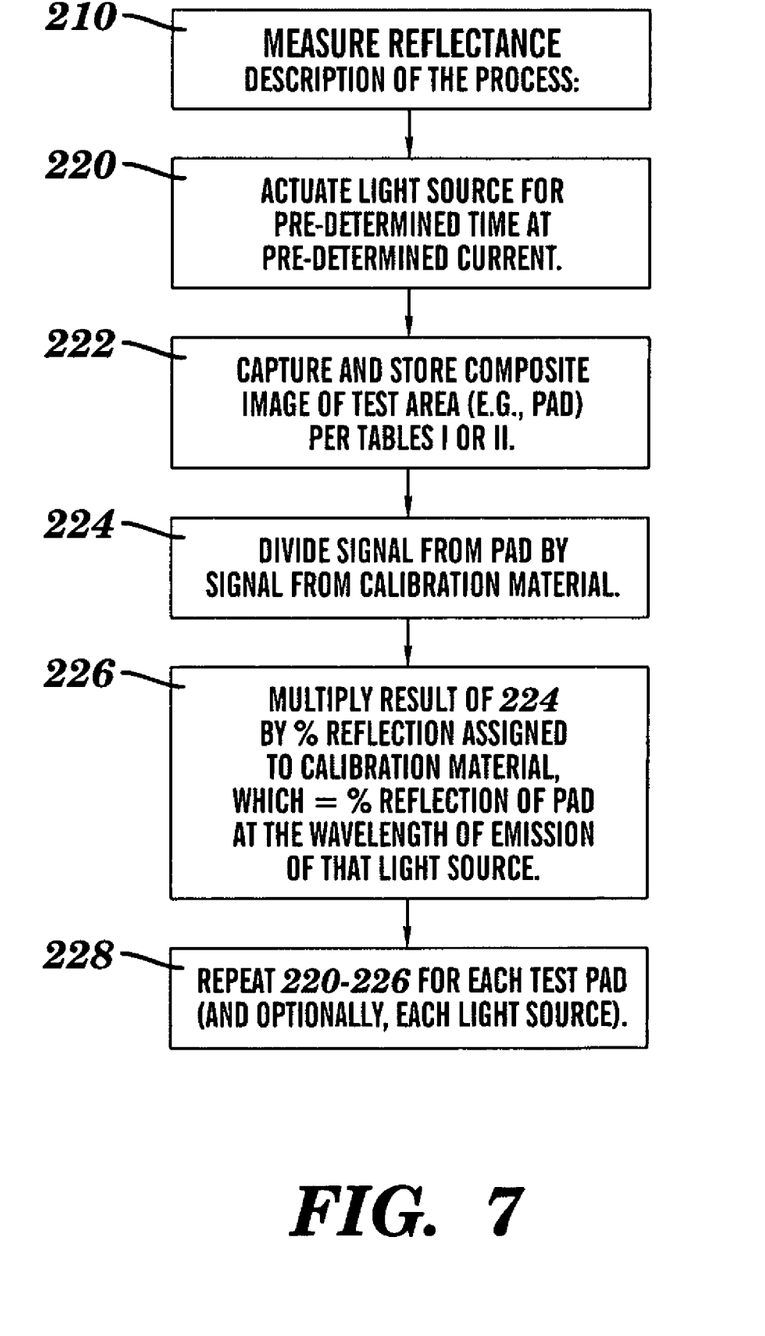
FIG. 7 is a flow chart of measurement steps effected during the operation of FIG. 6.

Turning now to FIG. 7, measurement 210 is discussed in greater detail. As shown, this measurement includes actuating light source 20 for a pre-determined time and pre-determined current (e.g., for electrically actuated light sources) at 220. This pre-determined time and current is preferably the same as that used during steps 203 and 205 of the calibration discussed above. The steps of Tables I and/or II are effected, including movement of the fields of view 72, 72', etc., relative to sample media 40, 40', etc., and signals received (i.e., images captured) by imagers 70, 70' are saved to memory 74 to form a composite image at 222. At 224, a numerical value of the reflectance of portions of the composite image are divided by a numerical equivalent of the reflectance value of the calibration material acquired at step 205 above. At 226, the result of 224 is multiplied by the known percent reflection of the calibration material to generate the percent reflection of the particular pad or portion of sample 40, etc., at the known wavelength of emission of the particular light source 64. This percent reflection corresponds to a color, which may be correlated to known diagnosis values as discussed above. As shown at 228, steps 220-226 may be repeated for each portion of interest of the sample media (e.g., each test pad), and optionally, for each light source, in the event light sources of distinct wavelengths (e.g., colors) are used.

In the preceding specification, the invention has been described with reference to specific exemplary embodiments thereof. It will be evident that various modifications and changes may be made thereunto without departing from the broader spirit and scope of the invention as set forth in the claims that follow. The specification and drawings are accordingly to be regarded in an illustrative rather than restrictive sense.

What is claimed is:

1. A readhead for a photometric diagnostic instrument, said readhead comprising:
   a housing adapted for incorporation within the photometric diagnostic instrument;
   an elongated sample table operatively engaged with said housing;
   said sample table configured to support elongated reagent sample media thereon, the sample media having a plurality of test areas disposed in spaced relation thereon, each of the test areas configured to react with a sample when disposed in contact with the sample and to change color according to an amount of a constituent or property in the sample;
   a light source configured to illuminate the sample table;
   an imager coupled to said housing;
   said imager having an elongated field of view;
   said elongated field of view including at least a portion of said sample table; and
   a scanning mechanism configured to move the field of view relative to the sample table; wherein said scanning mechanism comprises:
   a mirror disposed optically between the sample table and the imager;
   the mirror being supported by a pivotable mount; and
   an actuator coupled to the mirror;
   said actuator disposed to selectively pivot the mirror, wherein the field of view is moved relative to said elongated sample table.

2. The readhead of claim 1, wherein said readhead is for a photometric diagnostic instrument for illuminating a target area and receiving light from the target area, said readhead comprising:
   a first light source coupled to said housing, said first light source configured to emit light of a first wavelength;
   a second light source coupled to said housing, said second light source configured to emit light of a second wavelength;
   said elongated sample table having an aspect ratio of longitudinal to transverse dimension of at least 2:1;
   a light guide disposed to receive light from each of the light sources, and convey, when only one of said light sources is illuminated, substantially all of said light from said one light source towards the sample table; and
   an elongated image capture device coupled to receive light from the target area;
   the image capture device having an aspect ratio of longitudinal to transverse dimension of at least 2:1.

3. The readhead of claim 1, wherein said elongated sample table has an aspect ratio of longitudinal to transverse dimension of at least 2:1.

4. The readhead of claim 1, wherein the field of view has an aspect ratio of longitudinal to transverse dimension of at least 2:1.

5. The readhead of claim 1, wherein the sample media has an aspect ratio of longitudinal to transverse dimension of at least 2:1.

6. The readhead of claim 1, comprising a plurality of light sources, each configured to generate light of a distinct wavelength.

7. The readhead of claim 6, comprising a light guide disposed to receive light from each of the light sources, and to convey, when only one of said light sources is illuminated, substantially all of said light from said one light source to the target area so that said target area is illuminated substantially uniformly.

8. The readhead of claim 1, wherein said scanning mechanism is configured to move the field of view transversely relative to said elongated sample table.

9. The readhead of claim 1, wherein said actuator comprises a stepping motor.

10. The readhead of claim 1, comprising a memory device operatively engaged with said imager.

11. The readhead of claim 1, wherein said imager is configured to capture images of portions of the sample media during said movement of the field of view relative to the sample table.

12. The readhead of claim 11, wherein said captured images are stored to a memory device operatively associated with said imager to form a composite image.

13. The readhead of claim 12, comprising said memory device.

14. A readhead for a photometric diagnostic instrument, said readhead comprising:
   a housing adapted for incorporation within the photometric diagnostic instrument;
   an elongated sample table operatively engaged with said housing;
   said sample table configured to support elongated reagent sample media thereon, the sample media having a plurality of test areas disposed in spaced relation thereon, each of the test areas configured to react with a sample when disposed in contact with the sample and to change color according to an amount of a constituent or property in the sample;
   a light source configured to illuminate the sample table;
   an imager coupled to said housing;
   said imager having an elongated field of view;
   said elongated field of view including at least a portion of said sample table; and
   a scanning mechanism configured to move the field of view relative to the sample table; wherein said scanning mechanism comprises:
   an actuator coupled to the sample table;
   said actuator configured to move the sample table within a range of movement relative to said housing;
   said sample table configured to maintain the longitudinal dimension of the elongated sample media at an oblique angle relative to that of the field of view, throughout the range of motion.

15. The readhead of claim 14, wherein the longitudinal dimension of said elongated field of view is disposed obliquely relative to that of said sample table.

16. The readhead of claim 14, wherein the longitudinal dimension of the elongated sample media is disposed obliquely relative to that of said sample table.

17. The readhead of claim 14, wherein the imager is elongated, having a longitudinal dimension disposed obliquely relative to that of the elongated sample media.

18. The readhead of claim 14, wherein said actuator comprises a stepping motor.

19. A photometric diagnostic instrument comprising:
   a housing;
   an elongated sample table operatively engaged with said housing;
   said sample table configured to support elongated reagent sample media in a predetermined orientation thereon, the sample media having a plurality of test areas disposed in spaced relation thereon, each of the test areas configured to react with a sample when disposed in contact with the sample and to change color according to an amount of a constituent or property in the sample;

a light source configured to illuminate the sample table;
an elongated imager coupled to said housing;
said imager having an elongated field of view;
said elongated field of view including at least a portion of said sample table;
a scanning mechanism configured to move the field of view relative to the sample table, within a range of motion;
the imager configured to capture an image of a portion of the sample media disposed within said field of view;
a memory device coupled to said imager;
a processor coupled to said memory device and to said imager;
said processor configured to operate said scanning mechanism;
said imager configured to capture images of portions of the sample media during said movement of the field of view relative to the sample table;
said memory device configured to store captured images to form a composite image;
said processor configured to analyze said composite image;
said processor configured to derive a diagnosis value from said analysis, and to generate an output corresponding thereto; and
a sensor configured to detect limits of said range of motion.

20. The device of claim 19, wherein said diagnosis value comprises the amount of said constituent or property.

21. The device of claim 19, wherein said diagnosis value comprises a diagnosis of a condition.

22. The device of claim 19, wherein said sample media includes a test strip, and said test areas include test pads.

23. The device of claim 19, wherein the composite image includes substantially the entire test strip.

24. The device of claim 19, wherein said imager comprises an image capture device.

25. The device of claim 24, wherein said image capture device comprises a CCD device.

26. The device of claim 24, wherein said image capture device comprises a CMOS device.

27. The device of claim 24, wherein said array of imagers comprises a lens subsystem optically coupled thereto.

28. The device of claim 27, wherein said lens subsystem comprises a lens.

29. The device of claim 27, wherein said lens subsystem is configured to focus the images of portions of the sample media onto the image capture device.

30. The device of claim 19, wherein said memory device is configured for storing diagnostic data.

31. The device of claim 30, wherein said memory device is configured for storing calibration data.

32. The device of claim 19, wherein said sample media comprises a reagent cassette.

33. The device of claim 19, wherein said sample media comprises a microfluidic device.

34. The device of claim 19, wherein said sensor comprises said imager.

35. The device of claim 34, wherein said imager is configured to detect said limits by capturing at least one image.

36. A method for reading reagent sample media, the sample media having a plurality of test areas disposed in spaced relation thereon, each of the test areas configured to react with a sample when disposed in contact with the sample and to change color according to an amount of a constituent or property in the sample, the method comprising:

(a) receiving the sample media into a sample table associated with a readhead of a photometric diagnostic device, the sample table configured to maintain the sample media in a predetermined orientation thereto;
(b) moving a field of view of the imager relative to the sample table within a range of motion;
(c) capturing images of said test areas with the imager during said moving (b);
(d) aggregating said images to form a composite image;
(e) deriving said amount of said constituent or property in said sample from said analysis; and
(f) generating an output signal corresponding to said amount;
wherein said moving (b) comprises moving a mirror disposed optically between the imager and the sample media.

37. The method of claim 36, wherein said sample media is selected from the group consisting of test strips, reagent cassettes, and microfluidic devices.

38. The method of claim 36, further comprising the step of illuminating said sample media.

39. The method of claim 36, further comprising the step of calibrating the device.

40. The method of claim 39, wherein said calibrating comprises capturing an image of a calibration material of known reflectance.

41. The method of claim 40, wherein said deriving comprises:
dividing the reflectance of said image of said test pad by the reflectance of said image of a calibration material; and multiplying the result of said dividing by the known reflectance of the calibration material to generate a calibrated percent reflectance of the test pad.

42. The method of claim 41, wherein said deriving further comprises comparing the calibrated percent reflectance with known values of amounts of said constituent or property at various predetermined percent reflectances, to determine the amount of said constituent or property at said calibrated percent reflectance.

43. A method for reading reagent sample media, the sample media having a plurality of test areas disposed in spaced relation thereon, each of the test areas configured to react with a sample when disposed in contact with the sample and to change color according to an amount of a constituent or property in the sample, the method comprising:

(a) receiving the sample media into a sample table associated with a readhead of a photometric diagnostic device, the sample table configured to maintain the sample media in a predetermined orientation thereto;
(b) moving a field of view of the imager relative to the sample table within a range of motion;
(c) capturing images of said test areas with the imager during said moving (b);
(d) aggregating said images to form a composite image;
(e) deriving said amount of said constituent or property in said sample from said analysis; and
(f) generating an output signal corresponding to said amount; wherein said moving (b) comprises moving the sample table throughout a range of movement while maintaining the longitudinal dimension of the elongated sample media at an oblique angle relative to that of the field of view.

* * * * *